United States Patent [19]

Holmes et al.

[11] Patent Number: 5,383,895
[45] Date of Patent: Jan. 24, 1995

[54] ENDOSCOPIC SURGICAL GRASPER AND METHOD

[75] Inventors: Jeffrey E. Holmes; Jeffrey J. Christian, both of San Jose, Calif.

[73] Assignee: Unisurge, Inc., Cupertino, Calif.

[21] Appl. No.: 16,044

[22] Filed: Feb. 10, 1993

[51] Int. Cl.⁶ .............................................. A61B 17/28
[52] U.S. Cl. ................................................... 606/206
[58] Field of Search ................... 606/52, 53, 83, 170, 606/205–211, 174; 128/750–751, 858; 604/22

[56] References Cited

U.S. PATENT DOCUMENTS

| | | | |
|---|---|---|---|
| 1,785,919 | 12/1930 | Stickel et al. | 606/210 |
| 4,122,856 | 10/1978 | Mosior et al. | 606/174 |
| 4,944,741 | 7/1990 | Hasson | 606/206 |
| 5,009,661 | 4/1991 | Michelson | 606/170 |
| 5,201,739 | 4/1993 | Semm | 606/174 |
| 5,209,755 | 5/1993 | Abrahan et al. | 606/207 |
| 5,222,973 | 6/1993 | Sharpe et al. | 606/206 |

OTHER PUBLICATIONS

Ethicon Endo-Surgery, a Johnson and Johnson Company, "Hospital Price List," Feb. 24, 1992. P. 2-Straight Grasper, Code DSG21.

*Primary Examiner*—Stephen C. Pellegrino
*Assistant Examiner*—Wm. Lewis
*Attorney, Agent, or Firm*—Flehr, Hohbach, Test, Albritton & Herbert

[57] ABSTRACT

An endoscopic surgical grasper for use by the human hand comprising a handle adapted to fit into the human hand. A rigid tubular member having proximal and distal extremities is provided and has the proximal extremity secured to the handle in a predetermined position longitudinal of the handle. A push rod having proximal and distal extremities is slidably mounted in the tubular member. A stop is carried by the handle. A knob assembly is slidably mounted on said tubular member and is movable from a first position in engagement with the stop and a second position away from the stop longitudinal of the tubular member. The knob assembly includes a plunger slidably mounted on said tubular member. A pin and slot mechanism couples the plunger to the proximal extremity of the push rod and permits limited movement of said push rod longitudinally of the tubular member while preventing rotational movement of the plunger relative to the tubular member. The knob assembly also includes a knob rotatably mounted on said handle and threadedly engaging the plunger and has a portion adapted to engage the stop in the handle. A spring is disposed within the tubular member and yieldably urges the plunger and the push rod in a distal direction to the second position of said knob assembly. Jaw-like grasping members movable between open and closed positions are carried by the distal extremity of the tubular member. A linkage mechanism connects the first and second grasping members to the push rod.

6 Claims, 3 Drawing Sheets

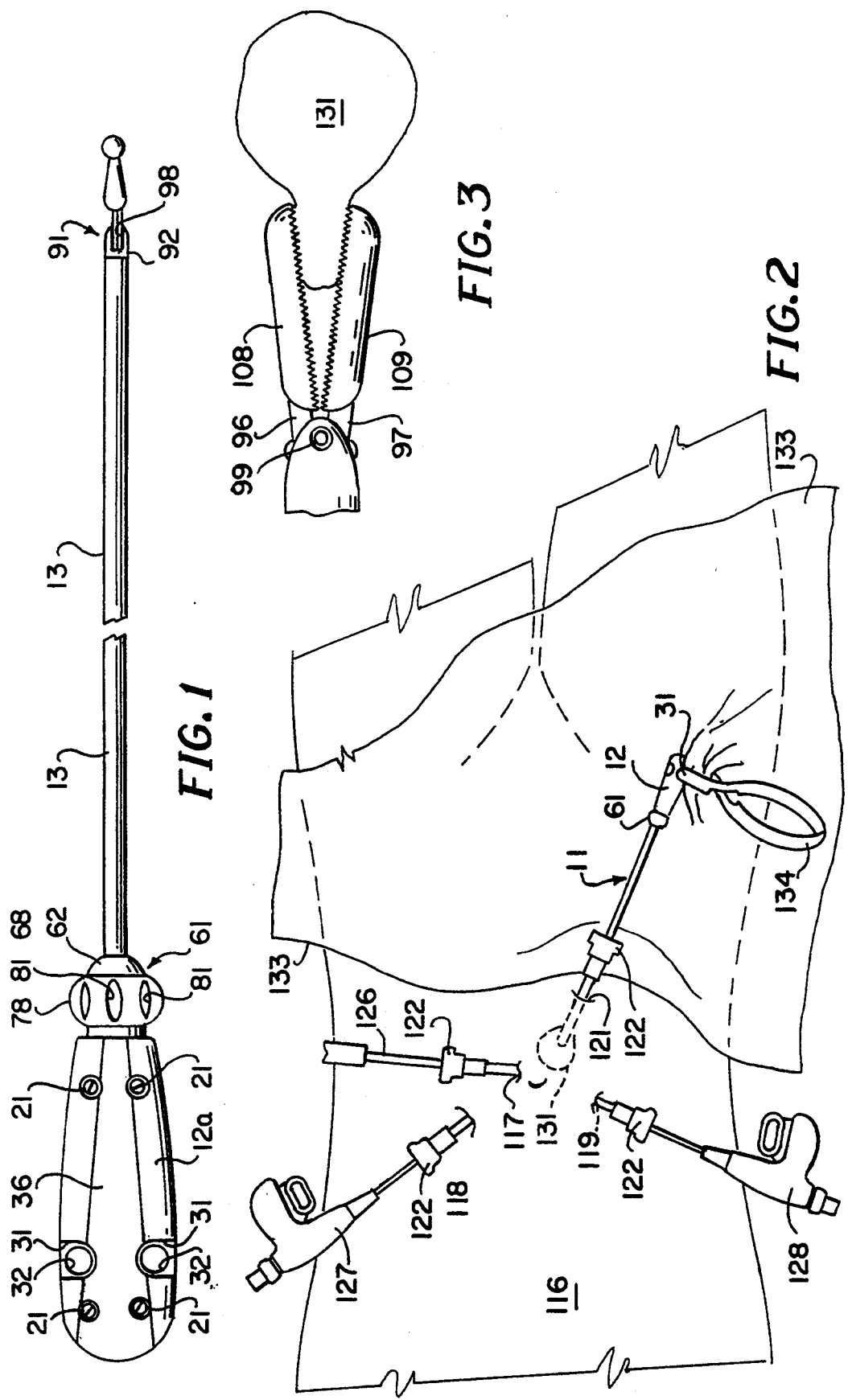

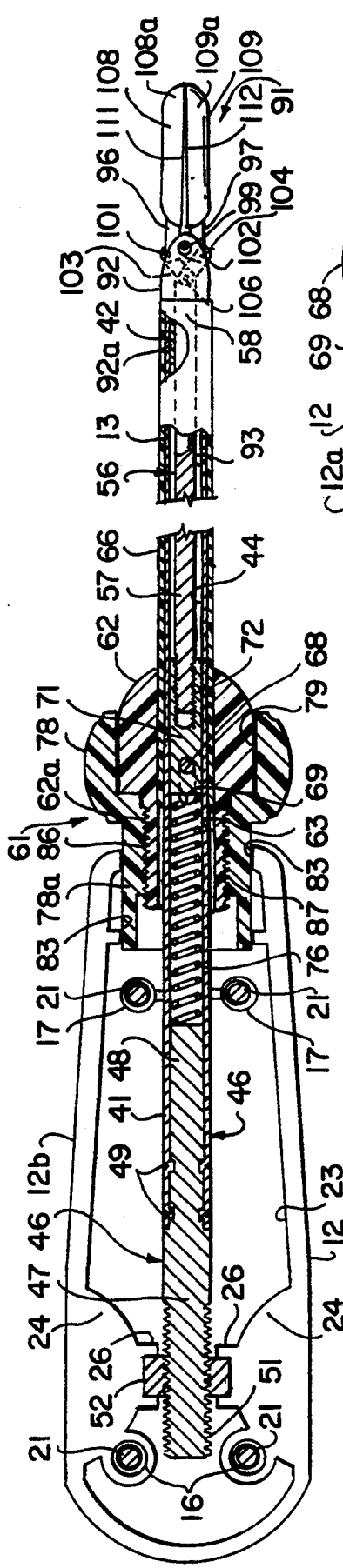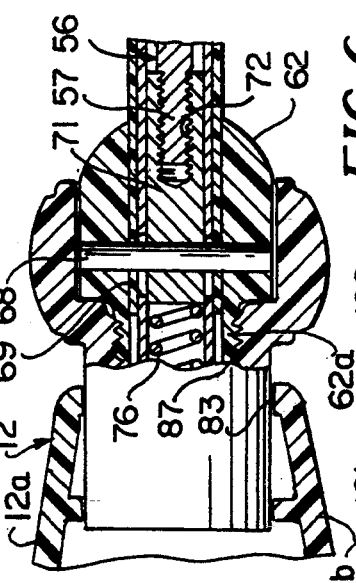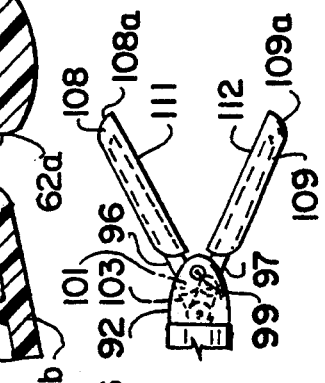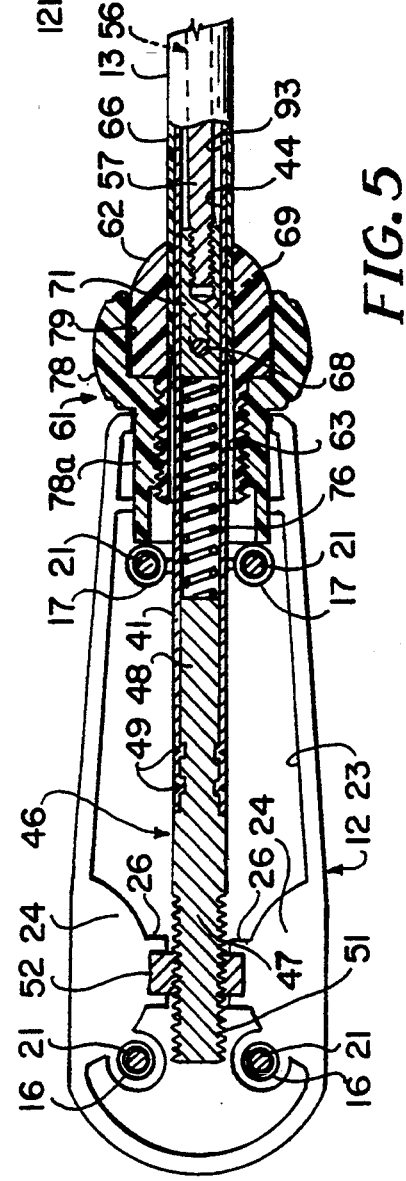
FIG. 4  FIG. 5  FIG. 6

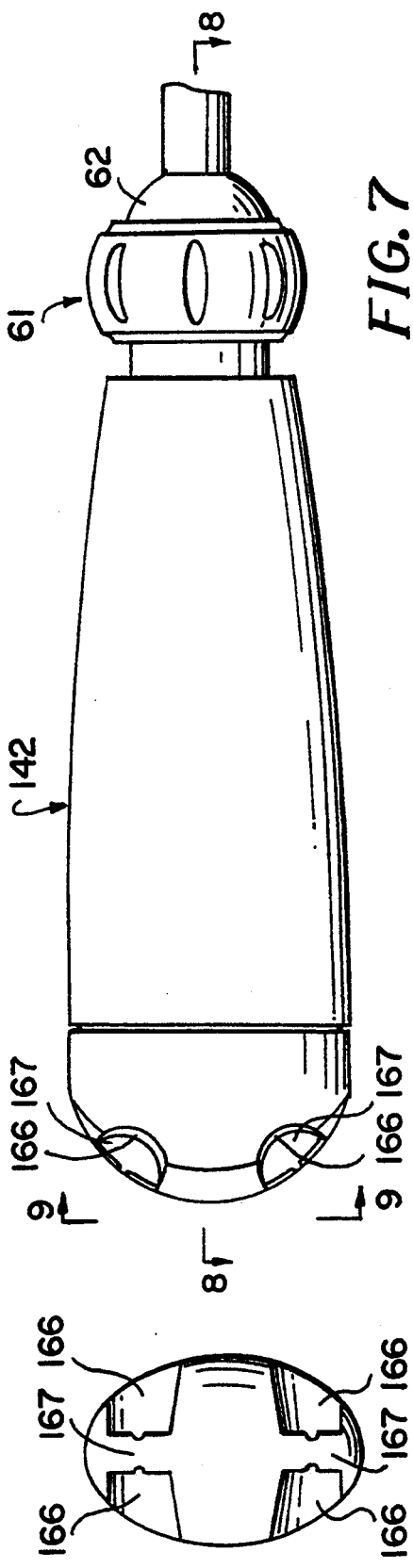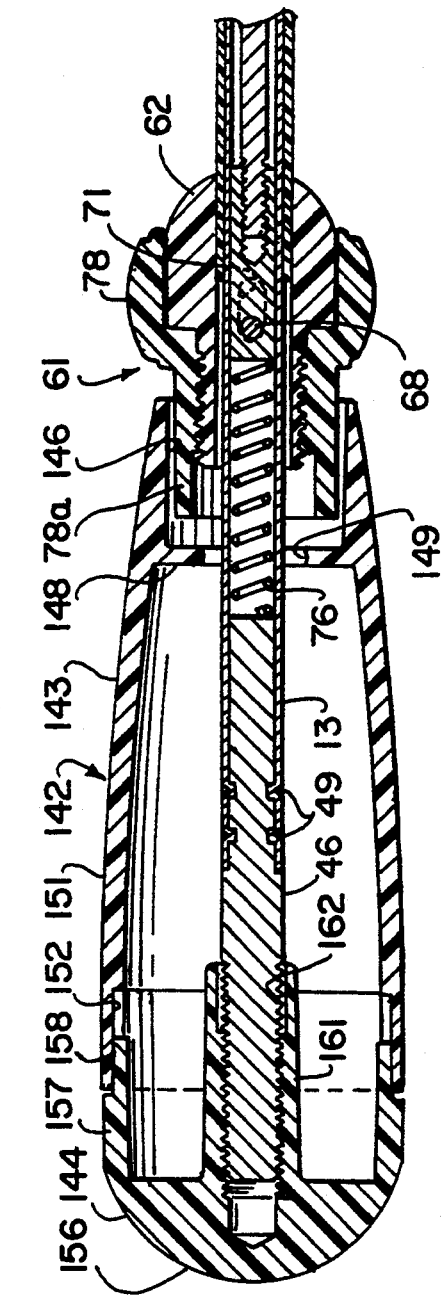

ENDOSCOPIC SURGICAL GRASPER AND METHOD

This invention relates to an endoscopic surgical grasper and method particularly in one useful in laparoscopic procedures.

Graspers have heretofore been provided. Such graspers often operate on a scissors principle and apply a certain amount of leverage based on the lever arm principle. With such devices, the grasping forces which can be generated are limited to those which can be provided by the doctor with the fingers of his hand. In certain type of procedures as for example, laparoscopic procedures involving removal of the gall bladder, such grasping forces may be inadequate, particularly if such grasping forces must be maintained over a period of time. There is therefore need for new and improved endoscopic surgical grasper and method which overcomes these disadvantages.

In general, it is an object of the present invention to provide an endoscopic surgical grasper and method which it makes it possible to provide increased grasping forces which can be sustained.

Another object of the invention is to provide a grasper and method of the above character which is particularly useful in laparoscopic procedures.

Another object of the invention is to provide a grasper and method of the above character which can be utilized and performed with the use of a single human hand.

Another object of the invention is to provide a grasper and method of the above character in which the grasping forces can be progressively increased.

Another object of the invention is to provide a grasper and method of the above character which is relatively simple in construction.

Additional objects and features of the invention will appear from the following description in which the preferred embodiments are set forth in detail in conjunction with the accompanying drawings.

FIG. 1 is a side elevational view of grasper incorporating the present invention.

FIG. 2 is a plan view illustrating a laparoscopic procedure utilizing the grasper and method of the present invention.

FIG. 3 is a view of the distal extremity of the grasper shown in FIGS. 1 and 2 grasping a gall bladder or other organ or tissue in the procedure shown in FIG. 2.

FIG. 4 is an enlarged side elevational view partially in cross section of the grasper shown in FIG. 1 in a closed position.

FIG. 5 is a view similar to FIG. 4 but showing the grasper in a open position.

FIG. 6 is a partial side elevational view of the grasper shown in FIG. 4 rotated by 90°.

FIG. 7 is a side elevational view of another embodiment of a handle for use on a grasper incorporating the present invention.

FIG. 8 is a cross-sectional view taken along the line 8—8 of FIG. 7.

FIG. 9 is an end elevational view looking along the line 9—9 of FIG. 7.

In general, the endoscopic surgical grasper for use by the human hand is comprised of a handle adapted to fit into the human hand. A rigid tubular member having proximal and distal extremities has the proximal extremity secured to the handle in a predetermined position longitudinal of the handle. Stop means is carried by the handle. A knob assembly is slidably mounted on the tubular member and is movable from a first position in engagement with the stop means to a second position away from the stop means longitudinal of the tubular member. The knob assembly includes a plunger slidably mounted on the tubular member. Pin and slot means is provided for coupling the plunger to the proximal extremity of the push rod permitting limited movement of the push rod longitudinally of the tubular member while preventing rotational movement of the plunger relative to the tubular member. The knob assembly also includes a knob rotatably mounted on the handle and threadedly engaging the plunger. Spring means is disposed within the tubular member and yieldably urges the knob assembly from said first position to said second position. Grasping means having first and second grasping members movable between open and closed positions is carried by the distal extremity of the tubular member. A toggle mechanism connects the first and second grasping members of the grasping means to the push rod whereby upon operation of the knob assembly, the grasping fingers can be moved between open and closed positions.

More in particular, as shown in the drawings, the endoscopic surgical grasper 11 for use by the human hand consists of a handle 12 and a rigid tubular member 13 which is carried by the handle. It should be appreciated that the endoscopic surgical grasper 11 of the present invention can be of the disposable type which can be disposed of after a one-time use. The handle 12 can be formed of a suitable material such as a plastic. One plastic found to be particularly suitable is ULTEM 1000 made by General Electric. This plastic is desirable because it can be radiation sterilized or autoclaved to make it possible to provide an endoscopic surgical grasper which can be reusable if not disposed of after use. The handle 12 is formed so that it is adapted to be grasped by a human hand. It can be formed of a one-piece multiconstruction or a two-piece multiconstruction having two parts 12a and 12b as shown in the drawings. Each of the parts 12a and 12b is provided with two sets of mating bosses 16 and 17 with the pair of bosses 16 being laterally aligned and spaced apart from the laterally aligned bosses 17. The bosses 16 and 17 and the two parts 12a and 12b are in registration with each other and are adapted to be fastened together by a suitable means such as screws 21. The parts 12a and 12b are provided with mating cavities 23 through which a pair of spaced-apart protrusions 24 extend. Spaced-apart parallel ears 26 are formed integral with the protrusions 24 and extend across the parts 12a and 12b and are in registration with each other and are used for a purpose hereinafter described. Spaced-apart pairs of cutouts 31 are formed in the protrusions 24 and extend from the handle 12 as shown particularly in FIG. 1. Circular recesses 32 are provided in the cutouts 31. Flats 36 are provided on the external surfaces of parts 12a and 12b and provide areas upon which an identifying mark for the grasper can be placed.

The tubular member 13 is provided with proximal and distal extremities 41 and 42. The tubular member is of a suitable length, as for example, 45 centimeters and has its proximal extremity 41 mounted within the handle 12 and secured therein in a predetermined fixed position longitudinal of the handle 12. The tubular member 13 is formed of a suitable material such as stainless steel and is provided with a bore 44 extending therethrough. An end piece or end bolt 46 is provided which has proximal and distal extremities 47 and 48. The distal extremity 47 is disposed within the bore 44 of the tubular member 13 and is retained therein by crimping the proximal extremity 41 of the tubular member 13 onto the end piece or end bolt 46 as shown by the spaced-apart parallel crimps 49. The proximal extremity 47 of the end piece or end bolt 46 is provided with threads 51 which are engaged by a square nut 52 which is seated between the ears 26 of the handle 12. The nut 52 is thus retained in a fixed longitudinal position of the tubular member 13. The longitudinal position of the tubular member 13 can be adjusted by rotating the threaded end piece 46 into and out of the nut 52 to the desired position and then can be fixed in the desired position by suitable means such as adhesive (not shown) placed between the nut 52 and the threads 51.

A push rod 56 formed of a suitable material such as stainless steel is slidably mounted in the bore 44 of the tubular member 13 and is provided with proximal and distal extremities 57 and 58.

A knob assembly 61 is slidably mounted on the tubular member 13 and is movable from a first position in engagement with the bosses 17 which serve as stop means within the handle 12 and a second position remote from the stop means longitudinal of the tubular member 13. The knob assembly 61 consists of the plunger 62 formed of a suitable material such as plastic. It is provided with a bore 63 permitting it be slidably mounted upon the tubular member 13. The tubular member 13 is provided with a sheath 66 extending over the outer surface of the tubular member 13 and is formed of a suitable material such as a heat-shrinkable plastic such as TEFLON which, for example can be colored a desirable color as for example, black. The bore 63 is of a size to accommodate the sheath 66 provided on the tubular member 13.

Pin and slot means is provided for coupling the plunger 62 to the push rod 56 permitting movement of the push rod 56 longitudinally of the tubular member 13 while preventing rotational movement of the plunger 62 relative to the tubular member 13 and consists of a pin 68 which is secured to and extends diametrically of the plunger 62 and a elongate slot 69 extending longitudinally of the tubular member 13 and provided in the tubular member and through which the pin 68 extends (see FIG. 5). The pin 68 also extends through a connector 71 which is slidably mounted within the bore 44 of the tubular member 13. The connector 71 is formed of suitable material such as stainless steel and has the proximal extremity 57 of the push rod secured therein by suitable means such as a threaded connection with a threaded bore 72. The slots 69 have a length which determines the extent of the movement of the plunger longitudinally of the tubular member 13. Yieldable spring means in the form of a coil spring 76 is disposed in the bore 44 of the tubular member 13 and has one end engaging the connector 71 and has the other end engaging the end piece or end bolt 46.

The knob assembly 61 also includes a knob 78 which is provided with a cylindrical bore 79 which receives the plunger 62 so that the knob 78 is rotatable with respect to the plunger 62. The outer surface of the knob 78 is provided with circumferentially spaced-apart indentations 81 to facilitate the grasping of the knob by the fingers of the hand. Means is provided for forming a threaded connection between the knob 78 and the plunger 62 and consists of a cylindrical extension 78a which is rotatably mounted in a bore 83 provided in the handle 12. The extension 78a extends over a cylindrical extension 62a provided on the plunger 62. Threads 86 on the extension 78a and threads 87 on the extension 62a form a threaded connection between the plunger 62 and the knob 78 which is used in a manner hereinafter described.

A grasping assembly 91 is mounted on the distal extremity 42 of the tubular member 13 and consists of a nose piece 92 formed of a suitable material such as stainless steel which is provided with a cylindrical extension 92a which is mounted within the distal extremity 42 of the tubular member 13 and is seated within the bore 44 and is retained therein by suitable means such as by a crimp fit (not shown). The nose piece 92 is provided with a bore 93 through which the push rod 56 extends. The grasping assembly 91 is of the type described in co-pending application, Ser. No. 07/806,666 filed on Dec. 13, 1991. As described therein it consists of the pair of arms or members 96 and 97 formed of a suitable material such as stainless steel which are pivotally mounted in a slot 98 provided in the nose piece 92 by pivot pin 99. The arms 96 and 97 are connected by pins 101 and 102 to links 103 and 104. The links 103 and 104 are pivotally connected to a distal extremity 58 of the push rod 56 by pin 106. By rectilinear movement of the push rod 56, the arms 96 and 97 can be moved between open and closed positions as shown in FIGS. 4 and 5. Jaws 108 and 109 are provided on the arms 96 and 97 and can be formed of a suitable plastic material such as ULTEM previously described which is molded onto the arms 96 and 97. The jaws 108 and 109 are formed with generally hemispherical end portions 108a and 109a to provide a rounded extremity for the jaws 108 and 109. The jaws 108 and 109 are provided with mating teeth 111 and 112 which extend along lines which are parallel to the arms 96 and 97 and are adapted to mate with each other with the distal teeth closing first as shown in FIG. 4 to permit a closing of the jaws 108 and 109 with respect to each other.

Operation and use of the endoscopic surgical grasper incorporating the present invention in performing the method may now be briefly described as follows. Let it be assumed that it is desired to perform a typical endoscopic procedure, as for example a laparoscopic cholecystectomy of a human being 116 by the use of four puncture sites 117, 118, 119 and 121 in the abdomen of the patient by the use of trocars and introducer assemblies 122 of the type described U.S. Pat. No. 5,176,648. An endoscope and camera 126 is provided in the site 117. A surgeon's instrument 127 and an assistant's instrument 128 are introduced into the sites 118 and 119 and are the type described in co-pending application, Ser. No. 07/806,666, filed Dec. 13, 1991. The endoscopic surgical grasper 11 of the present invention is introduced into the other site 121 and is to be utilized for grasping the gall bladder 131 of the patient. The surgeon or assistant while viewing the gall bladder through the endoscope 121 utilizes one hand to grasp the handle 12, as for example the right hand introduces it through the introducer 122 with the jaws 108 and 109 in their normally closed position and in which position they are normally yieldably retained by the action of the spring 76. The blunt rounded extremity of the closed jaws 108 and 109 makes it possible for the surgeon to readily move the distal extremity of the grasper into the desired position adjacent the gall bladder 131 to be removed. As soon as the distal extremity of the endoscopic surgical grasper 11 is in the desired position, the surgeon or assistant using the same hand, as for example the right hand holding the handle 12 utilizes the thumb and forefinger of the same hand to engage the knob 78 and to pull the knob 78 proximally towards the user and towards the handle 12 and to cause movement of the cylindrical portion 78a of the knob until the portion 78a comes into engagement with the stop means formed by the bosses 17. Movement of the knob 78 because of its threaded engagement with the plunger 62 causes proximal movement of the plunger 62 which carries with it the pin 68, the connector 71 and the push rod 57 connected thereto and brings the same proximally to the proximal ends of the slots 69 which also corresponds to the point at which the proximal extremity of the cylindrical portion 78a of the knob 78 engages the bosses 17. Proximal rearward or proximal movement of the push rod 58 pulls the pivot pin rearwardly to cause movement of the links 103 and 104 to cause operation of the toggle mechanism heretofore described to move the jaws 108 and 109 to the maximum open position at an angle of approximately 40° as shown in FIG. 5.

The surgical grasper 11 is then advanced with the jaws in an open position over the gall bladder 131 so that it is in a position to grasp the gall bladder. As soon as the gall bladder is within the jaws 108 and 109, the surgeon releases the knob 78 permitting the spring force provided by the spring 76 to move the push rod distally in a forward direction to cause the jaws 108 and 109 to grasp the tissue forming the gall bladder.

In order to prevent the gall bladder from escaping from between the jaws 108 and 109, additional closing or clamping pressure can be applied to the jaws 108 and 109 by the surgeon or assistant after the surgeon has released the knob 78 by rotating the knob 78 in a clockwise direction as viewed from the proximal end of the handle 12. Rotation of the knob 78 in the clockwise direction causes the cylindrical portion 78a to engage the stop provided by the bosses 17 and pushes plunger 62 distally to cause push rod 56 to be pushed or moved distally to cause further forces to be applied to the toggle mechanism to cause further closing of the jaws 108 and 109. This rotational movement of the knob 78 is continued by the surgeon until there is substantially increased resistance to rotation of the knob ensuring that the tissue of the gall bladder has been firmly compressed between the jaws 108 and 109 and clamped between the same, as for example as shown in FIG. 3 of the drawings. When this rotational position has been reached, the jaws 108 and 109 are firmly locked in these engaging positions because the cylindrical member 78a is in engagement with the stop provided by the bosses 17 preventing retraction of the plunger 62. With the gall bladder 131 firmly grasped in the grasper 11 the gall bladder 131 is then retracted to the desired position and handle 12 can then be clamped to the drape 133 being utilized on the patient by the use of a conventional towel clamp 134 engaging the drape 133 and the cutouts 31 provided on one side of the handle 12.

Because of the relatively long lever arm provided by the tubular member 13 of the endoscopic surgical grasper 11, it is relatively easy with a small amount of force applied to the handle 12 to pull back the gall bladder 131 and hold it in that position so that the desired additional endoscopic procedures can be readily performed for removal of the gall bladder. After the gall bladder has been dissected from the liver, it can be removed from the abdomen of the patient in a conventional manner. Alternatively it can be removed by the use of a retrieval device of the type described in co-pending application, Ser. No. 07/807,098, filed Dec. 13, 1991 by having the endoscopic surgical grasper 11 release the gall bladder into the retrieval device. This can be accomplished by the surgeon releasing the towel clamp 134 from the handle and grasping the handle 12. The knob 78 is rotated in a counterclockwise direction by the surgeon's fingers so that the cylindrical portion 78a is moved away from the stop means formed by the bosses 17. This permits the knob 78 to be pulled rearwardly by the thumb and forefinger of the surgeon's hand to pull the push rod 56 proximally or rearwardly to open the jaws 108 and 109 and to release the gall bladder 131. The endoscopic surgical grasper 11 can then be removed from the introducer 122 completing its use in the endoscopic procedure.

In FIGS. 7, 8 and 9 there is shown another handle 142 which can serve as another embodiment for the handle 12 as shown for the endoscopic surgical grasper 11. The handle 142 as shown therein consists of two parts 143 and 144 formed of a suitable molded plastic such as Ultem. The part 143 has a tapered generally cylindrical configuration which is adapted to fit within the palm of a human hand. It is provided with a cylindrical recess 146 which receives the cylindrical extension 78a of the knob 78. A radially-extending ledge 148 extends across the cylindrical recess 146 and has a centrally disposed hole 149 provided therein through which the tubular member 13 extends. The part 143 is provided with a cylindrical side wall 151 which is provided with an inner annular recess 152 near the proximal extremity thereof. The part 144 is formed of a cap and is provided with a spherical surface 156 and a depending cylindrical side wall 157 which has an outer annular recess 158 formed therein permitting the two parts 143 and 144 to mate with each other and to snap together to retain the same in a unitary assembly by cooperating protrusions and recesses (not shown) and applying a solvent or utilizing ultrasonic bonding. Alternatively an adhesive can be used for forming a permanent connection.

The part 144 is provided with a centrally disposed boss 161 which is formed integral therewith. The boss 161 is provided with internal threads 162 which are adapted to receive the threaded end piece 46. The exterior spherical surface 156 provided with spaced-apart pairs of outwardly facing notches 166 provided in opposite ends of the oval-shaped extremity as shown in FIG. 9. Transversely extending ribs 167 extend therebetween which are adapted to be grasped by a clamp (not shown) for holding the endoscopic surgical grasper in a desired position as hereinbefore described.

The operation and use of the endoscopic surgical grasper 11 having a handle 142 of the type shown in FIGS. 7, 8 and 9 can be utilized in the same manner as hereinbefore described in conjunction with the endoscopic surgical grasper 11 having the handle 12 thereon. The ledge 148 serves as stop means in the same manner as the bosses 17 in the handle 12 described in conjunction with the previous embodiment.

From the foregoing it can be seen that there has been provided an endoscopic surgical grasper and method which has a number of advantages. The grasper is a one-handed device that can be held by the palm of the hand while the fingers of the same hand can be utilized for operating the same. The desired amount of grasping forces can be readily applied and retained to firmly grasp tissue in between the jaws. Also it can be readily unlocked. It is provided with a relatively small handle so that it does not require much room in the operating arena. Although the jaws will grasp tissue rather firmly, it is done atraumatically because of the use of a polymeric material for the jaws as well as the large surface area provided by the jaws. Although the endoscopic surgical grasper has been described in conjunction with the removal of the gall bladder it should be appreciated that it can be readily utilized in connection with other organs of the human body, as for example intestines and the like. The device is also constructed in such a manner that it can be sterilized and reused if necessary. Also it is of relatively a simple construction making it possible to provide a device which is economical for one-time use.

What is claimed is:

1. An endoscopic surgical grasper for use by the human hand comprising a handle adapted to fit into the human hand, a rigid tubular member having proximal and distal extremities and having the proximal extremity secured to the handle in a predetermined position longitudinal of the handle, a push rod having proximal and distal extremities slidably mounted in the tubular member, stop means carried by the handle, a knob assembly slidably mounted on said tubular member and being movable from a first position in engagement with the stop means and a second position away from the stop means, said knob assembly including a plunger slidably mounted on said tubular member, pin and slot means coupling said plunger to the proximal extremity of the push rod and permitting limited movement of said push rod longitudinally of the tubular member while preventing rotational movement of the plunger relative to the tubular member, said knob assembly also including a knob rotatably mounted on said handle threadedly engaging said plunger and having a portion adapted to engage said stop means in said handle, spring means disposed within said tubular member and yieldably urging said plunger and the push rod in a distal direction towards said second position of said knob assembly, jaw-like grasping means having first and second members movable between open and closed positions carried by the distal extremity of the tubular member and a linkage mechanism connecting said first and second grasping members to said push rod.

2. A grasper as in claim 1 wherein said pin and slot means includes first and second slots and a pin disposed in the first and second slots said first and second slots being disposed in said tubular member and said pin being mounted in said plunger and being movable with said plunger.

3. A grasper as in claim 1 wherein said tubular member is provided with a bore and wherein said spring is disposed in said bore.

4. A grasper as in claim 1 wherein the tubular member is secured to the handle by an end piece secured in said bore and in the proximal extremity of said tubular member, a nut mounted in a fixed position in said handle and means forming a threaded connection between said nut and said end piece.

5. A grasper as in claim 1 wherein said stop means in said handle is comprised of a stop member provided in said handle and adapted to be engaged by the knob.

6. An endoscopic surgical grasper for use by the human hand comprising a handle adapted to fit into the hand, a rigid tubular member having proximal and distal extremities, means securing the proximal extremity of the rigid tubular member to the handle, jaw-like grasping means having first and second members movable between open and closed positions carried by the distal extremity of the rigid tubular member, a knob assembly carried by the handle, said knob assembly having first and second parts movable in a direction longitudinally of the tubular member and having another part which is rotatable with respect to the tubular member, means forming a threaded connection between the first and second parts and stop means carried by the handle adapted to be engaged by the second part, means connecting the first part of the knob assembly to the jaw-like grasping means whereby upon movement of the first part, the jaw-like grasping means can be moved between the open and closed positions when said first part engages the stop means and means carried by the tubular member whereby upon rotation of the another part of the knob assembly additional forces are applied to the jaw-like grasping means to non-yieldably urge the jaw-like grasping means towards a locked clamping position.

* * * * *